US00PP27041P3

(12) United States Plant Patent
Jacobs

(10) Patent No.: US PP27,041 P3
(45) Date of Patent: Aug. 9, 2016

(54) ***CHRYSANTHEMUM* PLANT NAMED 'ZANMUGLOW YELLOW'**

(50) Latin Name: ***Chrysanthemum×morifolium* Ramat.**
Varietal Denomination: Zanmuglow Yellow

(71) Applicant: Chrysanthemum Breeders Association Research B.V., Valkenburg ZH (NL)

(72) Inventor: Henricus Cornelius Maria Jacobs, Valkenburg (NL)

(73) Assignee: Chrysanthemum Breeders Association Research B.V., Valkenburg (NL)

( * ) Notice: Subject to any disclaimer, the term of this patent is extended or adjusted under 35 U.S.C. 154(b) by 3 days.

(21) Appl. No.: 14/544,365

(22) Filed: Dec. 30, 2014

(65) Prior Publication Data
US 2016/0192566 P1 Jun. 30, 2016

(51) Int. Cl.
*A01H 5/02* (2006.01)

(52) U.S. Cl.
USPC ..... Plt./289

(58) Field of Classification Search
USPC ..... Plt./289
CPC ..... A01H 5/0255; A01H 5/025
See application file for complete search history.

*Primary Examiner* — Kent L Bell
(74) *Attorney, Agent, or Firm* — Steptoe & Johnson LLP

(57) ABSTRACT

A *Chrysanthemum* plant named 'Zanmuglow Yellow' characterized by its medium sized blooms with yellow ray florets and prolific branching; natural season flower date September 22 (week 39); blooming for a period of 5 weeks.

3 Drawing Sheets

Botanical designation: *Chrysanthemum×morifolium* Ramat.

Cultivar denomination: 'Zanmuglow Yellow'.

RELATED CULTIVARS

The new plant is related to 'Zanmuglow' (U.S. Plant Pat. No. 22,617). 'Zanmuglow Yellow' is a mutant of 'Zanmuglow'.

BACKGROUND OF THE INVENTION

The present invention relates to a new and distinct cultivar of *Chrysanthemum* plant, botanically known as *Chrysanthemum×morifolium* Ramat., commercially known as a garden mum, and hereinafter referred to by the cultivar denomination 'Zanmuglow Yellow'. 'Zanmuglow Yellow' is a product of a selection program which had the objective of finding color mutants from existing parent plants. The new plant comprises a natural mutant of the parent *Chrysanthemum* named 'Zanmuglow'. Plants from the new cultivar 'Zanmuglow Yellow' differ from plants of the parent in (1) color of the ray-florets. And (2) Inflorescence size. (1) The color is yellow in the mutant, while it is white in the parent. (2). Inflorescences of the mutant are smaller in size than those of the parent.

The new and distinct cultivar was discovered and selected as a flowering plant by Henricus Cornelius Maria Jacobs on a cultivated field in Rijsenhout, The Netherlands in 2009. The first act of asexual production of 'Zanmuglow' was accomplished when vegetative cuttings from the initial selection in 2009 were propagated further in a controlled environment in Rijsenhout, The Netherlands. The new cultivar has been found to retain its distinctive characteristics through successive propagations.

BRIEF DESCRIPTION OF THE DRAWINGS

The present invention of a new and distinct variety of *Chrysanthemum* (of about 16 weeks) is shown in the accompanying drawings, the color being as nearly true as possible with color photographs of this type.

DESCRIPTION OF THE INVENTION

Figure 1:
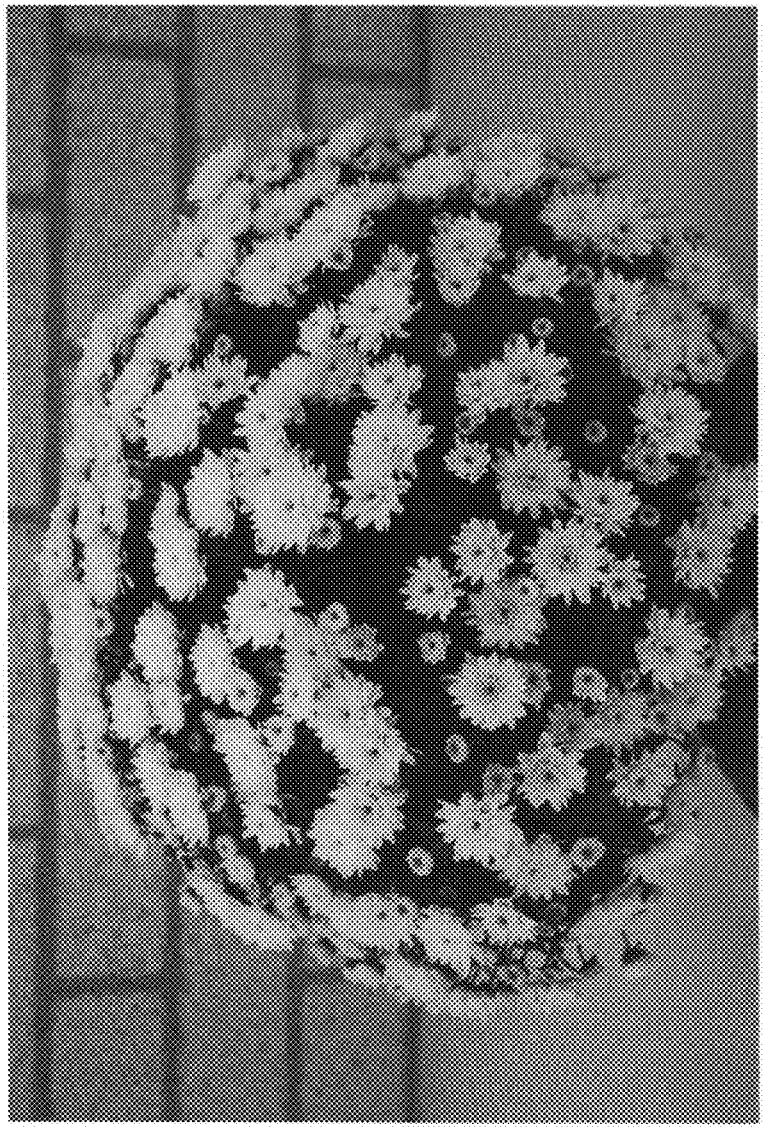
FIG. 1 shows a plant of the cultivar in full bloom.
Figure 2:
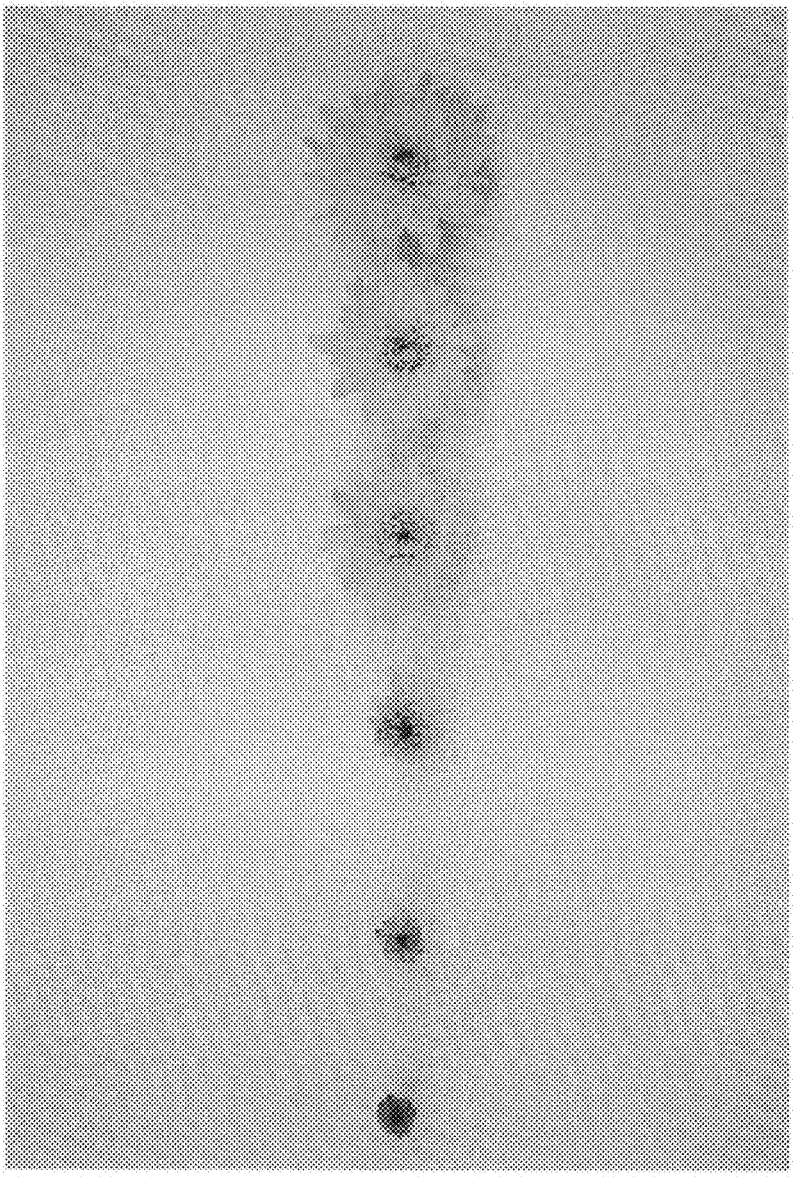
FIG. 2 shows the various stages of bloom of the new cultivar.
Figure 3:
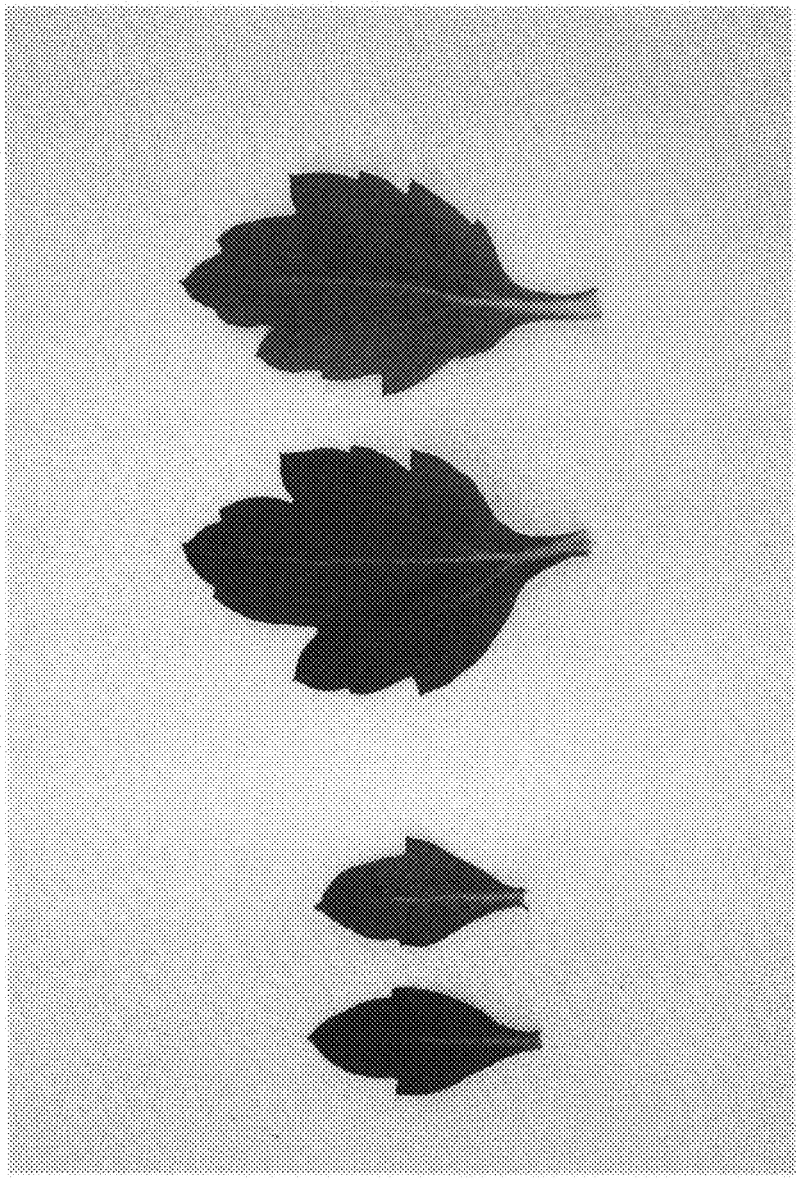
FIG. 3 shows the various stages of foliage of the new cultivar.

The observations and measurements were gathered from plants grown out door in Rijsenhout, The Netherlands under natural day length and temperature and planted in week 25 in 2014. The natural blooming date of this crop was September 22 (week 39). The average height of the plants was 30 cm. No growth retardants were used. No tests were done on disease or insect resistance or susceptibility. No tests were done on cold or drought tolerance. This new variety produces medium sized blooms with yellow ray florets blooming for a period of 5 weeks.

From the cultivars known to inventor the most similar existing cultivar in comparison to 'Zanmuglow Yellow' is 'Gold Crest' (U.S. Plant Pat. No. 11,606). When 'Gold Crest' and 'Zanmuglow Yellow' are being compared the following difference is noticed (1) Inflorescence size. And (2) Natural season blooming date. (1) Inflorescences of 'Gold Crest' are larger than those of 'Zanmuglow Yellow'. (2) Plants of 'Gold Crest' flower earlier in the season than those of 'Zanmuglow Yellow'.

The following is a description of the plant and characteristics that distinguish 'Zanmuglow Yellow' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

Botanical Description of *Chrysanthemum* × *morifolium* Ramat. 'Zanmuglow Yellow'

| | |
|---|---|
| **Bud** | |
| Size | Small; cross-section 5 mm, height 3 mm |
| Shape | Round |
| Texture | Pubescent |
| Outside Color | Greyed-green 191A |
| **Phyllaries** | |
| Number | 24, arranged in 3 rows |
| Shape | Elliptic |
| Apex | Acute |
| Base | Truncate |
| Margin | Entire |
| Color | Upper side: Green 139A<br>Lower side: Greyed-green 191A |
| Length and width | 4-5 mm; 1.5-2 mm |
| Texture | Pubescent |
| **Inflorescence** | |
| Type | Double |
| Height | 1.5 cm |
| Diameter | 4 cm |
| Peduncle length | 7 cm |
| Peduncle color | Greyed-Green 191B |
| Peduncle diameter | 1.8 mm |
| Peduncle texture | Pubescent |
| Number per branch | Approx 5 inflorescences |
| Duration of flowering | 5 weeks |
| Seeds | Produced in small quantities, ovate, Greyed-brown 199A, length 1.5 mm, diameter 0.5 mm |
| Fragrance | Faint chrysanthemum odor |
| **Color** | |
| Center of inflorescence (disc florets) | Immature stage: Yellow-Green 144A<br>Mature stage: Green-Yellow 1B |
| Color of upper surface of the ray-florets | Yellow 5A |
| Color of the lower surface of the ray-florets | Yellow 4B |
| Tonality from Distance | A garden mum with yellow flowers |
| Color of the ray-florets after aging of the plant | Yellow 13C |
| **Ray florets** | |
| Texture | Upper and lower surface smooth |
| Number | About 170 |
| Shape | Elliptic |
| Apex | Rounded |
| Base | Attenuate |
| Cross-section | Flat |
| Longitudinal axis of majority | Straight |
| Length of corolla tube | 2 mm |
| Ray-floret margin | Entire |
| Ray-floret length | 1.2-1.8 cm |
| Ray-floret width | 2-6 mm |
| Ratio length/width | Medium |
| **Disc florets** | |
| Disc diameter | 1-2 mm |
| Distribution of disc florets | Few, only visible in mature inflorescence |
| Shape | Tubular |
| Color | Yellow-green 145C at base to Green Yellow 1B at top |
| Length | 2 mm |
| Diameter | 0.8 mm |
| **Receptacle** | |
| Color | Yellow-green 145D |
| Shape | Domed raised |
| Height | 2 mm |
| Diameter | 3 mm |

TABLE 1-continued

Botanical Description of *Chrysanthemum* × *morifolium* Ramat. 'Zanmuglow Yellow'

| | |
|---|---|
| **Reproductive Organs** | |
| Androecium | Present on only disc florets |
| Stamen length | 3 mm |
| Stamen color | Yellow-green 144A |
| Anther color | Yellow 6D |
| Pollen | Present |
| Pollen color | Yellow 13A |
| Gynoecium | Present on both ray and disc florets |
| Style color | Yellow-green 154C |
| Style Length | 3 mm |
| Stigma color | Yellow 7A |
| Stigma Width | 1 mm |
| Ovary | Enclosed in calyx |
| **Plant** | |
| Form | Grown as a spray type pot mum, outdoor raised and mounded |
| Growth habit | Spherical shape |
| Growth rate | Medium |
| Height | 30 cm |
| Width | 45 cm |
| Stem Color | Greyed-brown 199A |
| Stem Strength | Strong |
| Stem Brittleness | Not brittle |
| Stem Anthocyanin Coloration | Not observed |
| Internode length | 1-1.5 cm |
| Length of lateral branch | From top to bottom 16 cm |
| Lateral branch color | Green 138A to 138B |
| Lateral branch, attachment | Medium |
| Lateral branch diameter | 2 mm |
| Branching (average number of lateral branches) | Prolific with 8 breaks after pinching |
| Natural season blooming date | September 22 (week 39) |
| **Foliage** | |
| Leaf color | Upper side: Green 139A<br>Lower side: Green 138A |
| Color midvein | Upper side: Yellow-green 147D<br>Lower side: Yellow-green 148D |
| Size | Small; length 2.5-3.8 cm, width 1.5-2.8 cm |
| Quantity (number per lateral branch) | About 20 |
| Shape | Elliptic |
| Texture upper side | Sparsely pubescent |
| Texture under side | Pubescent |
| Venation arrangement | Palmate |
| Shape of the margin | Serrated |
| Shape of Base of Sinus Between Lateral Lobes | Rounded |
| Margin of Sinus Between Lateral Lobes | Diverging |
| Shape of Base | Acute to truncate |
| Apex | Mucronulate |
| Petiole length | 2-4 mm |
| Petiole diameter | 2 mm |
| Petiole color | Yellow-green 147D |

TABLE 2

Differences with the comparison variety (when grown side to side)

| | 'Zanmuglow Yellow' | 'Gold Crest' |
|---|---|---|
| Inflorescence diameter | 4 cm | 5 cm |
| Natural season blooming date | week 39 | week 37 |

I claim:

1. A new and distinct *Chrysanthemum* plant named 'Zanmuglow Yellow' as described and illustrated.

* * * * *